(12) United States Patent
Fukuyama

(10) Patent No.: US 10,168,283 B2
(45) Date of Patent: Jan. 1, 2019

(54) OBSERVATION APPARATUS AND METHOD FOR SHARPENING FINAL IMAGE

(71) Applicant: OLYMPUS CORPORATION, Tokyo (JP)

(72) Inventor: Hiroya Fukuyama, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 178 days.

(21) Appl. No.: 15/410,828

(22) Filed: Jan. 20, 2017

(65) Prior Publication Data

US 2017/0131210 A1 May 11, 2017

Related U.S. Application Data

(63) Continuation of application No. PCT/JP2015/070970, filed on Jul. 23, 2015.

(30) Foreign Application Priority Data

Jul. 25, 2014 (JP) ................................ 2014-152347

(51) Int. Cl.
  *G02B 21/06* (2006.01)
  *G02B 26/10* (2006.01)
  (Continued)

(52) U.S. Cl.
  CPC ....... *G01N 21/6458* (2013.01); *G02B 21/006* (2013.01); *G02B 21/0032* (2013.01);
  (Continued)

(58) Field of Classification Search
  CPC ............ G01N 21/6458; G02B 21/0032; G02B 21/0048; G02B 21/006; G02B 21/0072; G02B 21/16
  (Continued)

(56) References Cited

U.S. PATENT DOCUMENTS 5,442,413 A 8/1995 Tejima et al.
5,815,301 A 9/1998 Naiki et al.
(Continued)

FOREIGN PATENT DOCUMENTS

EP 2983027 A1 2/2016
JP H06-265814 A 9/1994
(Continued)

OTHER PUBLICATIONS

International Search Report dated Oct. 20, 2015 issued in PCT/JP2015/070970.
(Continued)

*Primary Examiner* — James Greece
(74) *Attorney, Agent, or Firm* — Scully, Scott, Murphy & Presser, P.C.

(57) ABSTRACT

Acquiring a sharp final image by preventing, even when an intermediate image is formed at a position overlapping an optical element, a flaw or the like on the optical element from being superimposed on the intermediate image. An observation apparatus including: an image-forming optical system having image-forming lenses that form a final image and an intermediate image, a first phase modulator that applies a spatial disturbance to the wavefront of light, and a second phase modulator that cancels out the spatial disturbance; a light source; an XY-scanning part including a first and a second scanner; and a photodetector. The two phase modulators are disposed at positions optically conjugate with the first scanner and have one-dimensional phase-distribution characteristics changing in the scanning direction of the illumination light.

6 Claims, 6 Drawing Sheets

(51) Int. Cl.
*G01N 21/64* (2006.01)
*G02B 21/00* (2006.01)
*G02B 21/16* (2006.01)

(52) U.S. Cl.
CPC ..... *G02B 21/0048* (2013.01); *G02B 21/0072* (2013.01); *G02B 21/16* (2013.01); *G01N 2021/6478* (2013.01); *G01N 2201/0635* (2013.01)

(58) Field of Classification Search
USPC .......................................................... 359/618
See application file for complete search history.

(56) References Cited

U.S. PATENT DOCUMENTS

| | | | |
|---|---|---|---|
| 5,943,153 | A | 8/1999 | Naiki et al. |
| 6,738,195 | B2 | 5/2004 | Matsumoto et al. |
| 6,774,944 | B1 | 8/2004 | Fukuyama |
| 6,831,730 | B2 | 12/2004 | Matsumoto et al. |
| 8,482,637 | B2 | 7/2013 | Ohara et al. |
| 2003/0095342 | A1 | 5/2003 | Matsumoto et al. |
| 2004/0150879 | A1 | 8/2004 | Araki et al. |
| 2004/0160587 | A1 | 8/2004 | Matsumoto et al. |
| 2010/0110233 | A1 | 5/2010 | Ohara et al. |
| 2012/0063008 | A1* | 3/2012 | Jia ..................... G02B 27/0075 359/708 |
| 2013/0070217 | A1 | 3/2013 | Tatsuno |
| 2016/0025970 | A1 | 1/2016 | Fukuyama |

FOREIGN PATENT DOCUMENTS

| | | |
|---|---|---|
| JP | H08-292391 A | 11/1996 |
| JP | H10-257373 A | 9/1998 |
| JP | H11-109243 A | 4/1999 |
| JP | H11-211979 A | 8/1999 |
| JP | 2003-222795 A | 8/2003 |
| JP | 4011704 B2 | 11/2007 |
| JP | 2008-113860 A | 5/2008 |
| JP | 2008-245157 A | 10/2008 |
| JP | 2008-245266 A | 10/2008 |
| JP | 2008-268937 A | 11/2008 |
| JP | 2010-266813 A | 11/2010 |
| JP | 2013-083817 A | 5/2013 |
| WO | WO 2014/163114 A1 | 10/2014 |

OTHER PUBLICATIONS

International Search Report dated Oct. 13, 2015 issued in PCT/JP2015/070462.
International Search Report dated Oct. 13, 2015 issued in PCT/JP2015/070569.

* cited by examiner

OBSERVATION APPARATUS AND METHOD FOR SHARPENING FINAL IMAGE

CROSS-REFERENCE TO RELATED APPLICATIONS

This is a continuation of International Application PCT/JP2015/070970, with an international filing date of Jul. 23, 2015, which is hereby incorporated by reference herein in its entirety. This application claims the benefit of Japanese Patent Application No. 2014-152347, filed on Jul. 25, 2014, the content of which is incorporated herein by reference.

TECHNICAL FIELD

The present invention relates to an observation apparatus and a method for sharpening a final image.

BACKGROUND ART

A method for moving a focal position in a direction parallel to an optical axis by adjusting the optical path length at the intermediate image position is known (for example, see PTL 1).

CITATION LIST

Patent Literature

{PTL 1} The Publication of Japanese Patent No. 4011704

SUMMARY OF INVENTION

Technical Problem

In the method in PTL 1, because a plane mirror is disposed at the intermediate image plane, a flaw or foreign matter on the surface of the plane mirror may be superimposed on an image. When the method is applied to a microscope optical system, because the microscope optical system is a magnifying optical system, the longitudinal magnification is equal to the square of the transverse magnification, and thus, even a small movement of the focal position in the observation target in the direction parallel to the optical axis significantly moves the intermediate image in the optical axis direction thereof.

The present invention is an observation apparatus that enables a sharp final image to be acquired by preventing, even when an intermediate image is formed at a position overlapping an optical element, a flaw, foreign matter, defect, or the like on the optical element from being superimposed on the intermediate image, and provides a method for sharpening a final image.

Solution to Problem

An aspect of the present invention is an observation apparatus including: an image-forming optical system including a plurality of image-forming lenses that form a final image and at least one intermediate image, a first phase modulator that is disposed on an object side of any one of the intermediate images formed by the image-forming lenses and applies a spatial disturbance to a wavefront of light coming from an object, and a second phase modulator that is disposed at a position having at least one intermediate image between the second phase modulator and the first phase modulator and cancels out the spatial disturbance applied to the wavefront of the light coming from the object by the first phase modulator; a light source that is disposed on the object side of the image-forming optical system and generates illumination light to be incident on the image-forming optical system; a first scanner and a second scanner that are disposed at a distance from each other in the optical axis direction and scan the illumination light coming from the light source; and a photodetector that detects light emitted from an observation target disposed at a final image position of the image-forming optical system. The first phase modulator and the second phase modulator are disposed at positions optically conjugate with the first scanner, which is disposed on the light source side, and have one-dimensional phase-distribution characteristics changing in the direction equal to the direction in which the illumination light is scanned by the first scanner.

In this aspect, when the illumination light emitted from the light source enters the image-forming lenses from the object side, the illumination light is focused by the image-forming lenses and forms a final image. During this process, when the illumination light passes through the first phase modulator, which is disposed on the object side of one of the intermediate images, a spatial disturbance is applied to the wavefront of the illumination light, making the intermediate image to be formed blur and unsharp. Furthermore, when the illumination light after forming the intermediate image passes through the second phase modulator, the spatial wavefront disturbance applied by the first phase modulator is cancelled out.

In the above-described aspect, the first phase modulator and the second phase modulator may be lenticular elements.

In the above-described aspect, the first phase modulator and the second phase modulator may be prism arrays.

In the above-described aspect, the first phase modulator and the second phase modulator may be diffraction gratings.

In the above-described aspect, the first phase modulator and the second phase modulator may be cylindrical lenses.

Another aspect of the present invention is a method for sharpening a final image in an observation apparatus that includes: an image-forming optical system including a plurality of image-forming lenses that form a final image and at least one intermediate image; a light source that is disposed on the object side of the image-forming optical system and generates illumination light to be incident on the image-forming optical system; a first scanner and a second scanner that are disposed at a distance from each other in the optical axis direction and scan the illumination light coming from the light source; and a photodetector that detects light emitted from an observation target disposed at a final image position of the image-forming optical system. A first phase modulator that applies a spatial disturbance to a wavefront of the illumination light coming from the light source is disposed at a position that is on the object side of any one of the intermediate images formed by the image-forming lenses and that is optically conjugate with the first scanner, and a second phase modulator that has a one-dimensional phase-distribution characteristic changing in the direction equal to the direction in which the illumination light is scanned by the first scanner and that cancels out the spatial disturbance applied to the wavefront of the light coming from an object by the first phase modulator is disposed at a position that has at least one intermediate image between the second phase modulator and the first phase modulator and that is optically conjugate with the first scanner.

DESCRIPTION OF EMBODIMENTS

An observation apparatus 1 and a method for sharpening a final image according to an embodiment of the present invention will be described below with reference to the drawings.

The observation apparatus 1 according to this embodiment is, for example, a multiphoton excitation microscope.

Figure 1:
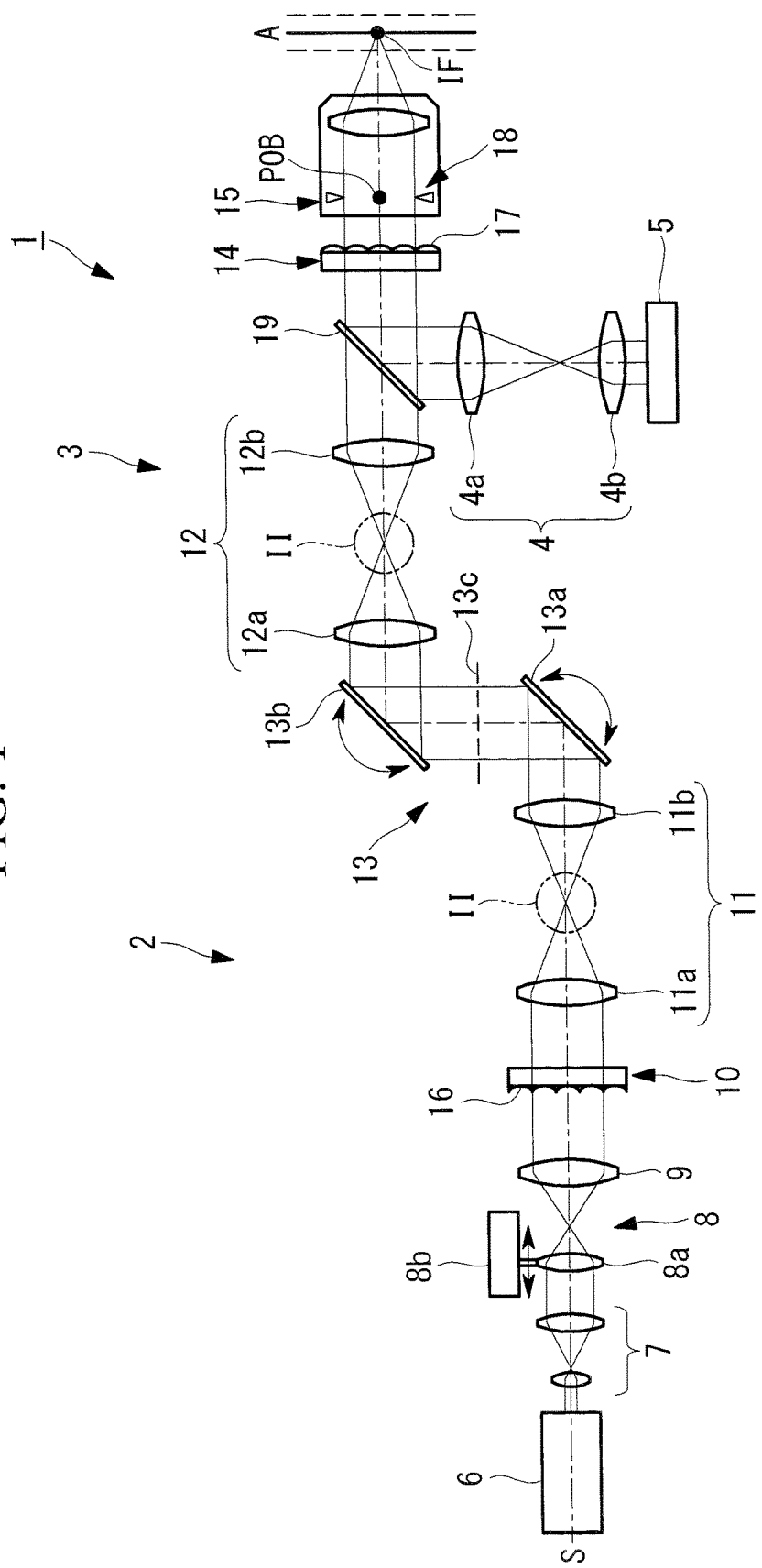
FIG. 1 is a schematic view showing an observation apparatus according to an embodiment of the present invention.

As shown in FIG. 1, the observation apparatus 1 includes an illumination device 2 that irradiates an observation target A with ultrashort-pulsed laser light (hereinbelow simply referred to as laser light (illumination light)), a detection optical system 4 that guides, to a photodetector 5, fluorescence generated in the observation target A by being irradiated with the laser light by the illumination device 2, and the photodetector 5 that detects the fluorescence guided by the detection optical system 4.

The illumination device 2 includes a light source 6 that generates laser light and an image-forming optical system 3 that irradiates the observation target A with the laser light coming from the light source 6.

The image-forming optical system 3 includes a beam expander 7 that increases the beam diameter of the laser light coming from the light source 6, a Z-scanning part 8 that forms an intermediate image by focusing the laser light passing through the beam expander 7 and moves the image forming position in the direction parallel to the optical axis S, and a collimating lens 9 that converts the laser light after passing through the Z-scanning part 8 and forming the intermediate image into substantially collimated light.

The image-forming optical system 3 also includes a wavefront disturbing element (first phase modulator) 10 disposed at a position through which the laser light converted into substantially collimated light by the collimating lens 9 passes, a plurality of relay lens pairs (image-forming lenses) 11 and 12 that relay the intermediate image formed by the Z-scanning part 8, an XY-scanning part 13 that is disposed between the relay lens pairs 11 and 12 and includes a galvanometer mirror (first scanner) 13a on the light source 6 side and a galvanometer mirror (second scanner) 13b on the observation target A side, a wavefront recovery element (second phase modulator) 14 disposed at a position through which the laser light converted into substantially collimated light by passing through the relay lens pairs 11 and 12 passes, and an objective lens (image-forming lens) 15 that focuses the laser light after passing through the wavefront recovery element 14, irradiates the observation target A with the laser light, and collects fluorescence generated at a laser-light focal point (final image IF) in the observation target A.

The Z-scanning part 8 includes a light-focusing lens 8a that focuses the laser light whose beam diameter has been magnified by the beam expander 7, and an actuator 8b that moves the light-focusing lens 8a in the direction parallel to the optical axis S. By moving the light-focusing lens 8a in the direction parallel to the optical axis S with the actuator 8b, it is possible to move the image forming position in the direction parallel to the optical axis S.

The wavefront disturbing element 10 is a lenticular element that is composed of an optically transparent material that can transmit light. The wavefront disturbing element 10 applies, when laser light passes therethrough, to the wavefront of the laser light, such phase modulation that changes in a one-dimensional direction perpendicular to the optical axis S according to the shape of the surface 16. In this embodiment, the necessary wavefront disturbance is applied by making the laser light coming from the light source 6 pass through the wavefront disturbing element 10 once.

The relay lens pair 11 is configured to focus the laser light converted into substantially collimated light by the collimating lens 9 with one lens 11a, forming an intermediate image II, and then focus the diverging laser light again with the other lens 11b such that the laser light is returned to substantially collimated light. In this embodiment, the two relay lens pairs 11 and 12 are disposed at a distance from each other with the XY-scanning part 13 disposed therebetween in the direction parallel to the optical axis S.

The galvanometer mirrors 13a and 13b are provided so as to be able to oscillate about axes that are perpendicular to the optical axis S and are skewed relative to each other. By making these galvanometer mirrors 13a and 13b oscillate, it is possible to change the inclination angle of the laser light in two-dimensional directions perpendicular to the optical axis S and, thus, to scan the position of the final image IF formed by the objective lens 15 in two-dimensional directions intersecting the optical axis S.

The wavefront recovery element 14 is a lenticular element that is composed of an optically transparent material that can transmit light, and has a phase-distribution characteristic opposite to that of the wavefront disturbing element 10. The wavefront recovery element 14 applies, when laser light passes therethrough, to the wavefront of the light, such phase modulation that changes only in a one-dimensional direction perpendicular to the optical axis S according to the shape of the surface 17, thereby cancelling out the wavefront disturbance applied by the wavefront disturbing element 10.

In this embodiment, the two galvanometer mirrors 13a and 13b are disposed at a distance from each other in the direction parallel to the optical axis S and are disposed such that an intermediate position 13c therebetween is disposed at a position substantially optically conjugate with a pupil position POB of the objective lens 15.

Figure 2:
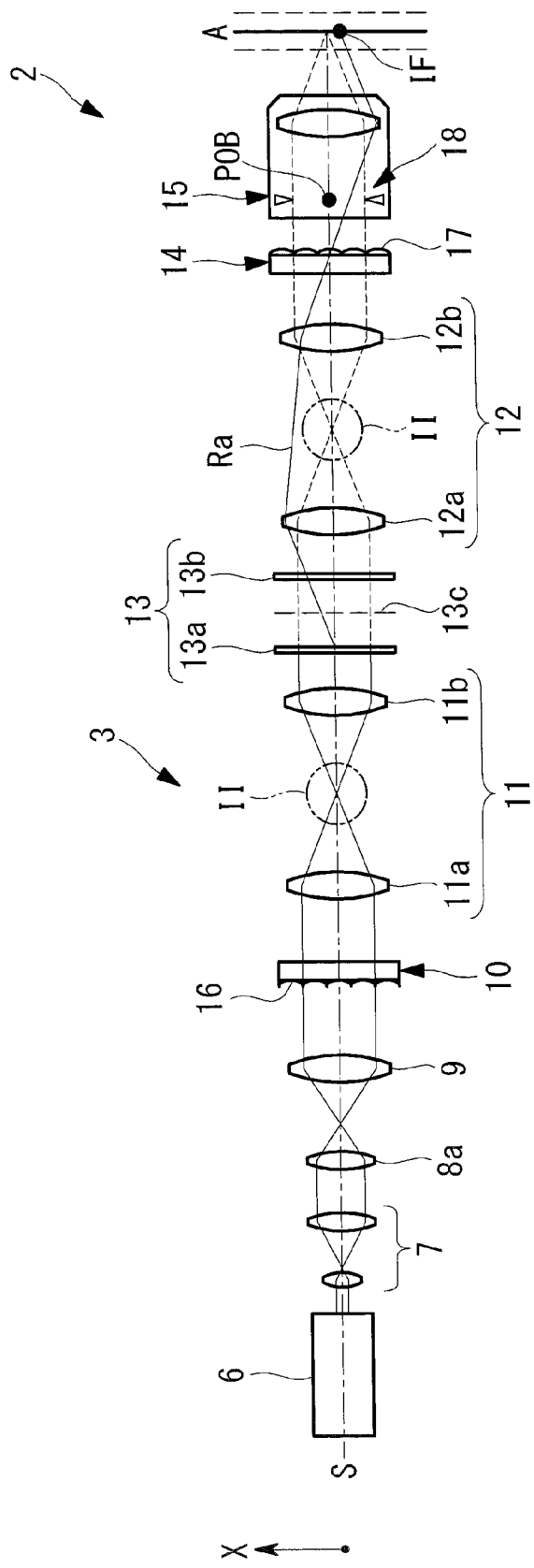
FIG. 2 is a plan view showing an illumination device in FIG. 1.

Furthermore, the galvanometer mirror 13a on the light source 6 side is disposed at a position optically conjugate with the wavefront disturbing element 10 and the wavefront recovery element 14. With this configuration, even when the galvanometer mirror 13a on the light source 6 side is made to oscillate, thus applying an inclination angle to the laser light, a central ray Ra of the laser light beam P intersects the optical axis S on the surface 17 of the wavefront recovery element 14, as shown in FIG. 2. Specifically, the laser light beam P is made to pass through the same region without changing the passing position in the wavefront recovery element 14.

The galvanometer mirror 13a is disposed such that the oscillation direction thereof (arrow X direction in FIG. 2) is equal to the direction in which the phase-distribution characteristic of the wavefront recovery element 14 changes. As has been described above, because the laser light beam P passes through the same region of the wavefront recovery element 14 regardless of the oscillation of the galvanometer mirror 13a, even when the galvanometer mirror 13a oscillates, the phase modulation to be applied to the laser light does not need to be changed.

Figure 3:
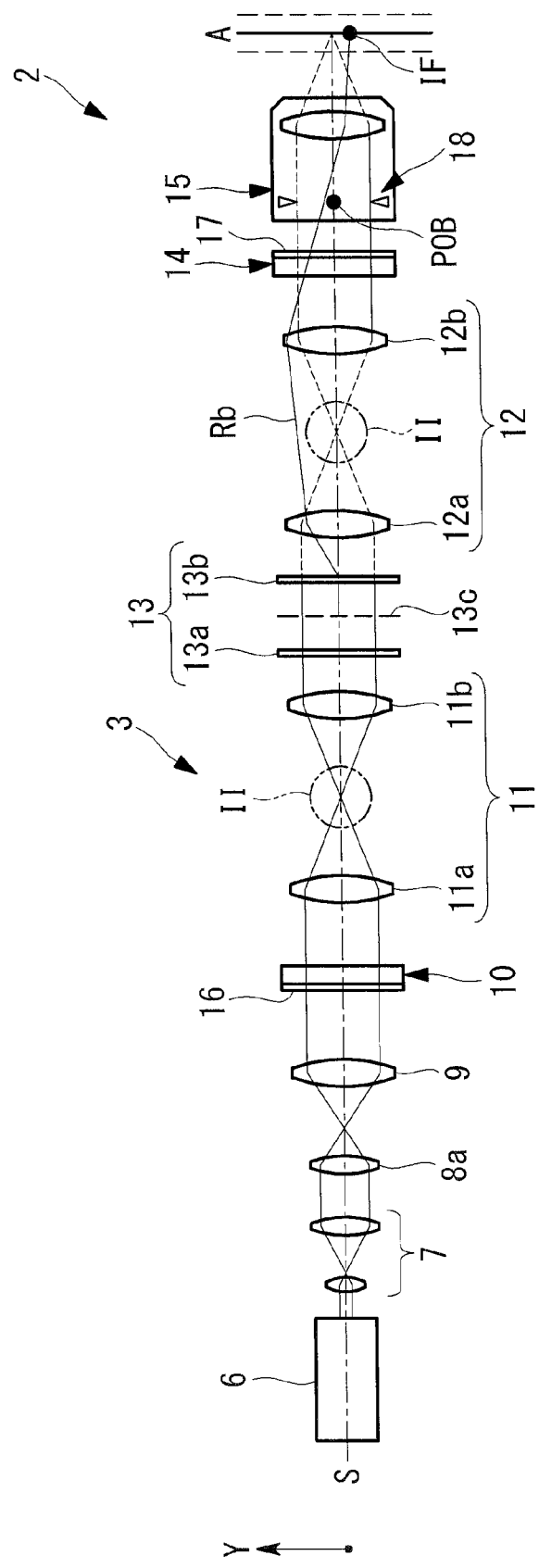
FIG. 3 is a side view showing the illumination device shown in FIG. 1.
Figure 4:
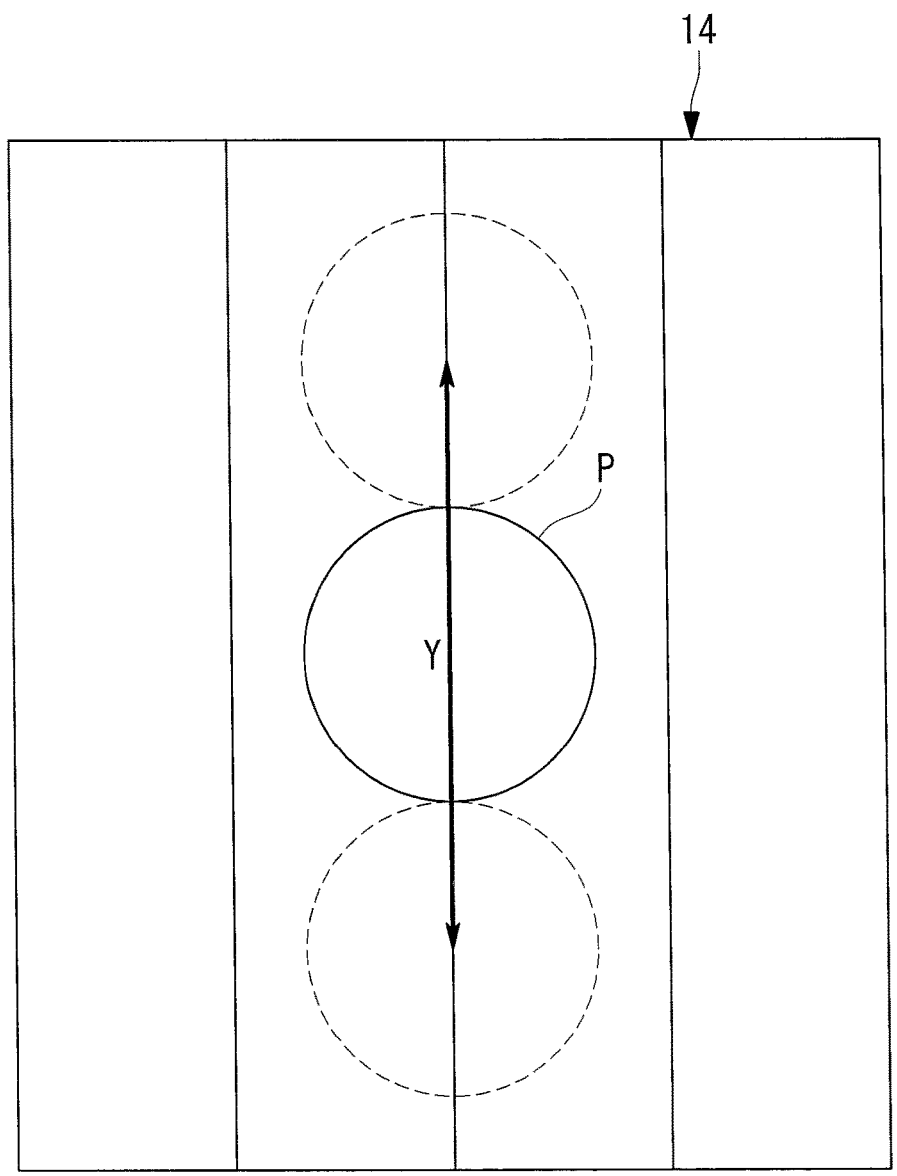
FIG. 4 is a lateral sectional view showing the passing position of a beam in a scanning movement of the wavefront recovery element in FIG. 1.

On the other hand, the galvanometer mirror 13b on the observation target A side is disposed at a position optically non-conjugate with the wavefront recovery element 14. With this configuration, when the galvanometer mirror 13b on the observation target A side is made to oscillate, applying an inclination to the laser light, the central ray Rb of the laser light beam P moves away from the optical axis S on the surface of the wavefront recovery element 14, as shown in FIG. 3. The galvanometer mirror 13b is disposed such that the oscillation direction thereof (arrow Y direction in FIG. 3) is equal to the direction perpendicular to the direction in which the phase-distribution characteristic of the wavefront recovery element 14 changes (the direction in which the phase-distribution characteristic does not change). With this configuration, when the galvanometer mirror 13b on the observation target A side is made to oscillate, and the inclination corresponding to this oscillation is applied to the laser light coming from the galvanometer mirror 13a on the light source 6 side, as shown in FIG. 4, due to the inclination applied to the laser light, the passing position of the laser light beam P in the wavefront recovery element 14 moves in the direction in which the phase-distribution characteristic of the wavefront recovery element 14 does not change.

Figure 5:
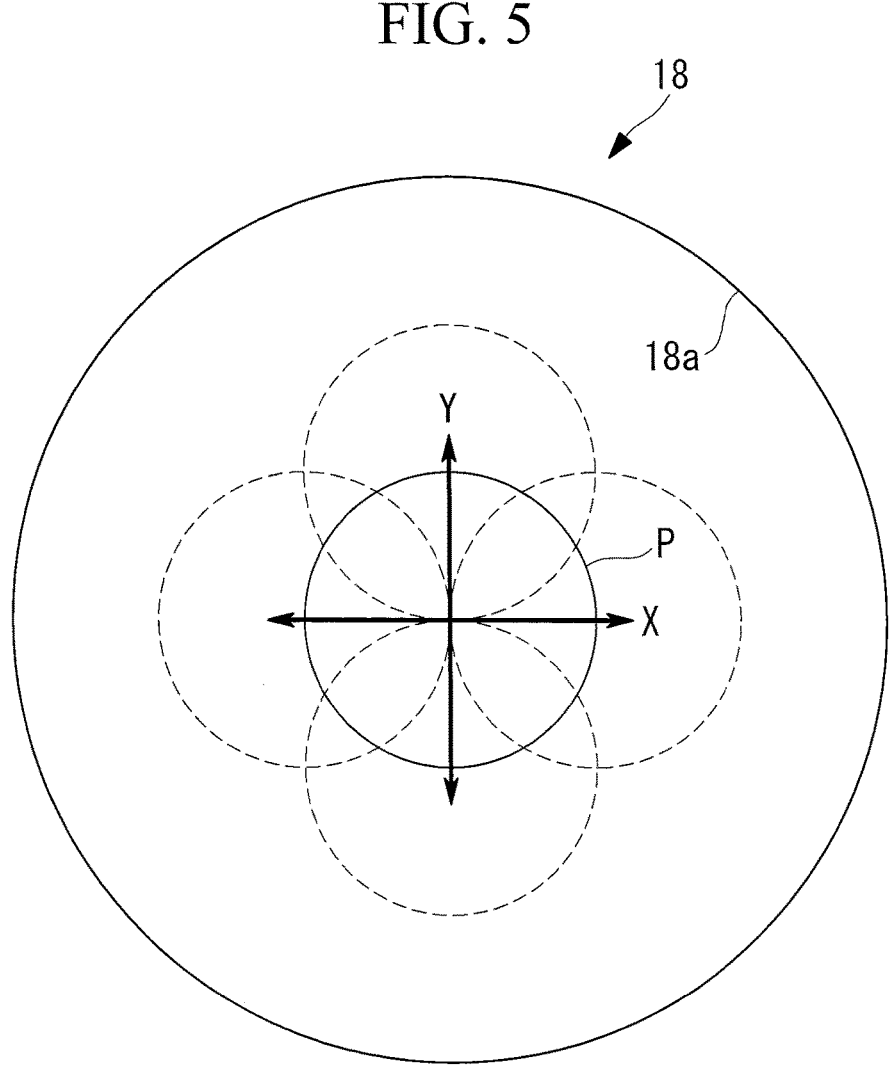
FIG. 5 is a lateral sectional view showing the passing position of the beam in a scanning movement at a pupil position of the objective lens in FIG. 1.

Note that, as has been described above, because the galvanometer mirrors 13a and 13b are both disposed at positions non-conjugate with the pupil position POB of the objective lens 15, the oscillations of the galvanometer mirrors 13a and 13b move the laser light beam P in two-dimensional (arrow X and arrow Y) directions at the pupil position POB of the objective lens 15, as shown in FIG. 5. However, the moving range thereof is limited to movement within a very small range in which it can pass without being vignetted by an opening 18a of an aperture stop 18 disposed at the pupil position POB of the objective lens 15.

The detection optical system 4 includes a dichroic mirror 19 that splits off the fluorescence collected by the objective lens 15 from the optical path of the laser light, and two light-focusing lenses 4a and 4b that focus the fluorescence split off by the dichroic mirror 19.

The photodetector 5 is, for example, a photomultiplier tube and detects the intensity of the incident fluorescence.

The operation of the thus-configured observation apparatus 1 according to this embodiment will be described below.

When an observation target A is to be observed with the observation apparatus 1 according to this embodiment, the laser light emitted from the light source 6 is radiated on the observation target A via the image-forming optical system 3. The laser light is first increased in beam diameter by the beam expander 7 and is then made to pass through the Z-scanning part 8, the collimating lens 9, and the wavefront disturbing element 10.

The laser light is focused by the light-focusing lens 8a of the Z-scanning part 8, and the light-focusing position can be adjusted in the direction parallel to the optical axis S by the actuation of the actuator 8b.

Furthermore, by making the laser light pass through the wavefront disturbing element 10, a spatial disturbance is applied to the wavefront thereof.

Thereafter, the laser light is made to pass through the two relay lens pairs 11 and 12 and the XY-scanning part 13, whereby it forms an intermediate image II and the inclination angle of the beam P is changed, and then passes through the dichroic mirror 19. Then, the laser light after passing through the dichroic mirror 19 passes through the wavefront recovery element 14, where the spatial disturbance applied by the wavefront disturbing element 10 is cancelled out, and is then focused by the objective lens 15, forming a final image IF on the observation target A.

The laser-light focal position, which is the position of the final image IF formed by the image-forming optical system 3, can be moved in the direction parallel to the optical axis S by moving the light-focusing lens 8a by actuating the actuator 8b. By doing so, the observation depth in the observation target A can be adjusted. Furthermore, by making the galvanometer mirrors 13a and 13b oscillate, it is possible to two-dimensionally scan, in directions perpendicular to the optical axis S, the laser-light focal position in the observation target A.

Regarding the laser light to which the spatial wavefront disturbance is applied by the wavefront disturbing element 10, even after a plurality of intermediate images II are formed by the relay lens pairs 11 and 12, one beam P is divided into a large number of small beams and is provided with astigmatism due to the effect of the lenticular element, that is, a cylindrical lens array, constituting the wavefront disturbing element 10. As a result, a point image, which is originally one, is unsharpened and formed as an aggregation of a large number of circular images, elliptical images, or linear images arranged on a straight line. Because the spatial wavefront disturbance applied by the wavefront disturbing element 10 is cancelled out by the laser light passing through the wavefront recovery element 14, it is possible to obtain a sharp image in the formation of the final image IF, which occurs downstream of the wavefront recovery element 14.

Specifically, as a result of the intermediate image II being unsharpened and blurred, even when the intermediate image II is located near an optical element having a flaw, foreign matter, defect, or the like on the surface or inside thereof, it is possible to prevent the flaw, foreign matter, defect, or the like from being superimposed on the intermediate image II, and thus making the final image IF formed on the observation target A unsharp. As a result, it is possible to form an extremely small spot image as the final image IF.

In this case, although the laser light beam P moves in a one-dimensional linear direction due to the oscillation of the galvanometer mirror 13a on the light source 6 side, the beam P in the wavefront recovery element 14, which is located at a position optically conjugate with the galvanometer mirror 13a, passes through the same region in the arrow X direction. Accordingly, regardless of the oscillation of the galvanometer mirror 13a, the phase modulation applied to the laser light by the wavefront recovery element 14 does not need to be changed.

On the other hand, when the galvanometer mirror 13b on the observation target A side is made to oscillate, the inclination of the laser light beam P is changed by the oscillation of the galvanometer mirror 13b, moving the passing position of the beam P in the wavefront recovery element 14 in the arrow Y direction. Because the arrow Y direction is equal to the direction in which the phase-distribution characteristic of the wavefront recovery element 14 does not change, even when the beam P passes through other regions of the wavefront recovery element 14 in the arrow Y direction due to the movement of the passing position of the beam P, the phase modulation to be applied does not change. Accordingly, even when the galvanometer mirror 13b oscillates, the phase modulation applied to the laser light by the wavefront recovery element 14 does not need to be changed.

As a result, even when the two galvanometer mirrors 13a and 13b are made to oscillate to scan the laser light in two-dimensional directions, it is possible to constantly apply predetermined phase modulation with the wavefront recovery element 14 without being influenced by the scanning state of the laser light and thus to completely cancel out the spatial wavefront disturbance applied by the wavefront disturbing element 10.

Then, as a result of an extremely small spot image being formed on the observation target A, it is possible to increase the photon density in an extremely small region to generate fluorescence, and, by collecting the generated fluorescence with the objective lens 15, splitting it off with the dichroic mirror 19, and guiding the fluorescence to the photodetector 5 with the detection optical system 4, it is possible to detect the fluorescence.

As a result of the fluorescence intensity detected by the photodetector 5 being stored in association with a three-dimensional laser-light scanning position, using a position in the arrow X and Y directions scanned by the galvanometer mirrors 13a and 13b and a position in the direction parallel to the optical axis S scanned by the actuator 8b, a fluorescence image of the observation target A is acquired. Specifically, the observation apparatus 1 according to this embodiment has an advantage in that, because it causes fluorescence to be generated in an extremely small spot region at each scanning position, it is possible to acquire a fluorescence image having high spatial resolution.

Furthermore, in the observation apparatus 1 according to this embodiment, because there is no need to provide a relay lens pair between the two galvanometer mirrors 13a and 13b, the number of components of the apparatus can be reduced. Furthermore, by employing a configuration in which the galvanometer mirrors 13a and 13b are disposed adjacent to each other without providing a relay lens pair, the size of the apparatus can be reduced.

Note that, in this embodiment, although lenticular elements have been shown as examples of the wavefront disturbing element 10 and the wavefront recovery element 14, instead, elements having one-dimensional phase-distribution characteristics may be employed. For example, prism arrays, diffraction gratings, cylindrical lenses, or the like may be employed.

Furthermore, in this embodiment, although the galvanometer mirrors 13a and 13b have been shown as examples of the first scanner and the second scanner, one or both of them may be replaced with another type of scanner. For example, a polygon mirror, an AOD (acoustooptical device), a KTN (Potassium-Tantalate-Niobate) crystal, or the like may be employed.

Furthermore, although a multiphoton excitation microscope has been shown as an example of the observation apparatus 1 according to this embodiment, instead, the observation apparatus 1 may be applied to a confocal microscope.

By doing so, an extremely small spot image is formed as a sharpened final image IF on the observation target A, whereby it is possible to increase the photon density in an extremely small region to generate fluorescence. Thus, it is possible to increase the fluorescence passing through the confocal pinhole and thus to acquire a bright confocal image.

Furthermore, instead of the observation apparatus 1 serving as the confocal microscope and detecting the fluorescence passing through the confocal pinhole, it may detect the light passing through the confocal pinhole and reflected or scattered at the observation target A.

Furthermore, in this embodiment, although the present invention has been described as the observation apparatus 1, the present invention may be understood as a method for sharpening a final image.

Specifically, the method for sharpening a final image according to an embodiment of the present invention is a method for sharpening a final image IF in a typical laser-scanning multiphoton excitation microscope, which is the observation apparatus 1 shown in FIG. 1 without the wavefront disturbing element 10 and the wavefront recovery element 14.

In the method for sharpening a final image according to this embodiment, the wavefront disturbing element 10 is disposed at a position between the galvanometer mirror 13a on the light source 6 side and the light source 6, the position being optically conjugate with the galvanometer mirror 13a, and the wavefront recovery element 14 is disposed at a position behind the objective lens 15, the position being optically conjugate with the galvanometer mirror 13a on the light source 6 side. The wavefront recovery element 14 is disposed such that the phase-distribution characteristic thereof is equal to the direction (arrow X direction) in which the laser light is scanned by the galvanometer mirror 13a.

With this method for sharpening a final image, it is possible to cancel out, with the wavefront recovery element 14, the spatial wavefront disturbance applied by the wavefront disturbing element 10, regardless of the oscillation angles of the galvanometer mirrors 13a and 13b. Thus, the intermediate image II is unsharpened, making it possible to prevent the image of foreign matter located at the image forming position of intermediate image II from being superimposed on the intermediate image II and to sharpen the final image IF. Specifically, there is an advantage that it is possible to sharpen the final image IF and acquire an image having high spatial resolution solely by adding the wavefront disturbing element 10 and the wavefront recovery element 14 to an existing typical scanning multiphoton excitation microscope.

Figure 6:
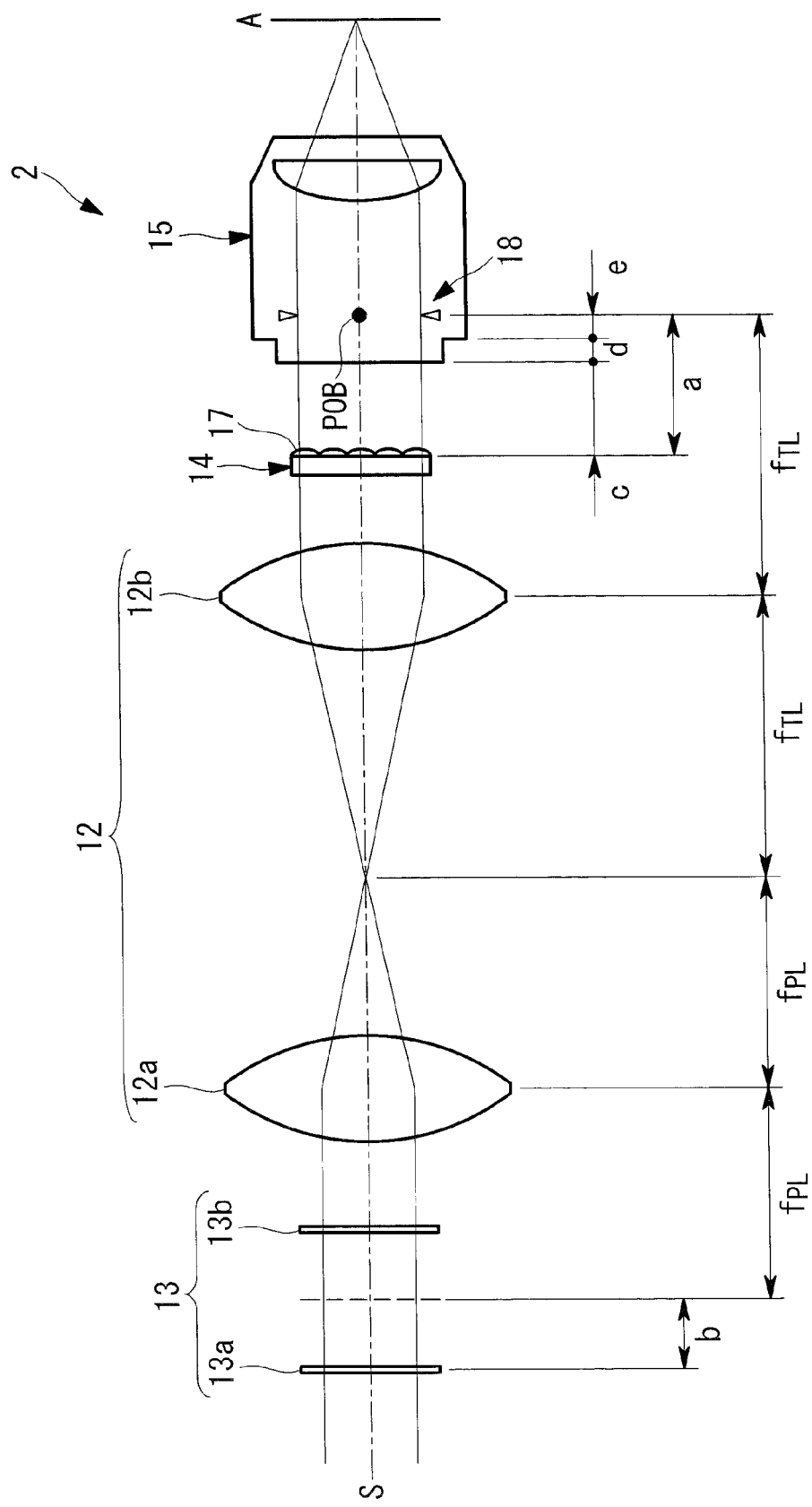
FIG. 6 is an enlarged schematic view showing a portion of an illumination device according to an example of the present invention.

Next, an example of the observation apparatus 1 according to this embodiment will be described below, using FIG. 6.

The observation apparatus 1 according to this embodiment includes the illumination device 2, the detection optical system 4, and the photodetector 5.

Furthermore, the distance a between the pupil position POB of the objective lens 15 and the wavefront recovery element 14 satisfies the condition in Expression (1).

$$a = b(fTL/fPL)^2 \quad (1)$$

where b is the distance between the galvanometer mirror 13a on the light source 6 side and a position 13c, which is located between the two galvanometer mirrors 13a and 13b and is substantially conjugate with the pupil position POB of the objective lens 15; fPL is the focal length of a lens 12a, on the light source 6 side, of the relay lens pair 12; and fTL is the focal length of a lens 12b, on the observation target A side, of the relay lens pair 12.

Furthermore, the distance c between the rear end of the screw of the objective lens 15 and the wavefront recovery element 14 satisfies the condition in Expression (2).

$$c = a - (d+e) \quad (2)$$

where d is the amount of projection of the screw of the objective lens 15, and e is the distance between the abutting surface of the objective lens 15 and the pupil position POB of the objective lens 15.

Values in this example are as follows:
b=2.7 (mm)
fPL=52 (mm)
fTL=200 (mm)
d=5 (mm)
e=28 (mm).

Accordingly, from Expression (1), a=39.9 (mm) is calculated, and from Expression (2), c=6.9 (mm) is calculated. As a result, the wavefront recovery element 14 is disposed at a position behind the objective lens 15 and optically conjugate with the galvanometer mirror 13a on the light source 6 side, without touching the outer frame of the objective lens 15.

According to the above described embodiment of the observation apparatus, by blurring and unsharpening the intermediate image, even when the intermediate image is located near an optical element having a flaw, foreign matter, defect, or the like on the surface or inside thereof, it is possible to prevent the occurrence of an inconvenience that a flaw, foreign matter, defect, or the like is superimposed on the intermediate image and is eventually formed as a part of the final image.

By two-dimensionally scan the illumination light coming from the light source with the first scanner and the second scanner, the final image formed on the observation target can be two-dimensionally scanned. In this case, when the first scanner is actuated, the illumination light beam moves in a one-dimensional linear direction. However, because the first scanner and the second phase modulator are disposed at positions optically conjugate with each other, the position of the beam passing through the second phase modulator does not change.

On the other hand, the second scanner, which is disposed at a distance from the first scanner in the optical axis direction, is not disposed at a position optically conjugate with the second phase modulator. Hence, when the second scanner is actuated, the illumination light beam moves so as to change the passing position in the second phase modulator. Because the direction in which the phase-distribution characteristic of the second phase modulator changes is equal to the direction in which the illumination light is scanned by the first scanner, the phase-distribution characteristic does not change in the direction perpendicular thereto, that is, the scanning direction of the illumination light with the second scanner. Thus, even when the passing position of the illumination light beam changes, the phase modulation applied to the illumination light does not change.

Accordingly, in this embodiment, regardless of which of the first scanner and the second scanner, which are disposed at a distance from each other in the optical axis direction, is actuated, it is possible not to change the phase modulation by the second phase modulator and maintain a constant state without being influenced by the scanning state of the illumination light, and it is possible to completely cancel out the spatial wavefront disturbance applied by the first phase modulator.

REFERENCE SIGNS LIST

1 observation apparatus
3 image-forming optical system
5 photodetector
6 ultrashort-pulsed laser light (light source)
10 wavefront disturbing element (first phase modulator)
11 and 12 relay lens pairs (image-forming lens)
13 XY scanning part
13a galvanometer mirror (first scanner)
13b galvanometer mirror (second scanner)
14 wavefront recovery element (second phase modulator)
15 objective lens (image-forming lens)

The invention claimed is:

1. An observation apparatus comprising:
   an image-forming optical system including a plurality of image-forming lenses that form a final image and at least one intermediate image, a first phase modulator that is disposed on an object side of any one of the intermediate images formed by the image-forming lenses and applies a spatial disturbance to a wavefront of light coming from an object, and a second phase modulator that is disposed at a position having at least one intermediate image between the second phase modulator and the first phase modulator and cancels out the spatial disturbance applied to the wavefront of the light coming from the object by the first phase modulator;
   a light source that is disposed on the object side of the image-forming optical system and generates illumination light to be incident on the image-forming optical system;
   a first scanner and a second scanner that are disposed at a distance from each other in the optical axis direction and scan the illumination light coming from the light source; and
   a photodetector that detects light emitted from an observation target disposed at a final image position of the image-forming optical system,
   wherein the first phase modulator and the second phase modulator are disposed at positions optically conjugate with the first scanner, which is disposed on the light source side, and have one-dimensional phase-distribution characteristics changing in the direction equal to the direction in which the illumination light is scanned by the first scanner.

2. The observation apparatus according to claim 1, wherein the first phase modulator and the second phase modulator are lenticular elements.

3. The observation apparatus according to claim 1, wherein the first phase modulator and the second phase modulator are prism arrays.

4. The observation apparatus according to claim 1, wherein the first phase modulator and the second phase modulator are diffraction gratings.

5. The observation apparatus according to claim 1, wherein the first phase modulator and the second phase modulator are cylindrical lenses.

6. A method for sharpening a final image in an observation apparatus that includes: an image-forming optical system including a plurality of image-forming lenses that form a final image and at least one intermediate image; a light source that is disposed on the object side of the image-forming optical system and generates illumination light to be incident on the image-forming optical system; a first scanner and a second scanner that are disposed at a distance from each other in the optical axis direction and scan the illumination light coming from the light source; and a photodetector that detects light emitted from an observation target disposed at a final image position of the image-forming optical system, wherein
   a first phase modulator that applies a spatial disturbance to the wavefront of the illumination light coming from the light source is disposed at a position that is on the object side of any one of the intermediate images formed by the image-forming lenses and that is optically conjugate with the first scanner, and a second phase modulator that has a one-dimensional phase-distribution characteristic changing in the direction equal to the direction in which the illumination light is scanned by the first scanner and that cancels out the spatial disturbance applied to the wavefront of the light coming from an object by the first phase modulator is disposed at a position that has at least one intermediate image between the second phase modulator and the first phase modulator and that is optically conjugate with the first scanner.

* * * * *